United States Patent
Yee et al.

(10) Patent No.: US 11,051,705 B2
(45) Date of Patent: Jul. 6, 2021

(54) BLOOD PRESSURE AND CARDIAC MONITORING SYSTEM AND METHOD THEREOF

(71) Applicant: Robert Bosch GmbH, Stuttgart (DE)

(72) Inventors: Seow Yuen Yee, Mountain View, CA (US); Christian Peters, Los Altos, CA (US); Thomas Rocznik, Mountain View, CA (US); Fabian Henrici, Los Altos, CA (US); Franz Laermer, Weil der Stadt (DE)

(73) Assignee: Robert Bosch GmbH, Stuttgart (DE)

( * ) Notice: Subject to any disclaimer, the term of this patent is extended or adjusted under 35 U.S.C. 154(b) by 743 days.

(21) Appl. No.: 15/834,686

(22) Filed: Dec. 7, 2017

(65) Prior Publication Data

US 2018/0092533 A1 Apr. 5, 2018

Related U.S. Application Data

(63) Continuation-in-part of application No. 15/564,585, filed as application No. PCT/EP2017/058487 on Apr. 10, 2017.
(Continued)

(51) Int. Cl.
*A61B 5/02* (2006.01)
*A61B 5/021* (2006.01)
(Continued)

(52) U.S. Cl.
CPC ............ *A61B 5/021* (2013.01); *A61B 5/0006* (2013.01); *A61B 5/0022* (2013.01);
(Continued)

(58) Field of Classification Search
CPC ................ G16H 50/20; A61B 5/02108; A61B 5/04012; A61B 5/0402
See application file for complete search history.

(56) References Cited

U.S. PATENT DOCUMENTS

2014/0221859 A1 8/2014 Albert
2014/0257056 A1 9/2014 Moon et al.
(Continued)

FOREIGN PATENT DOCUMENTS

WO 2015/0120330 A1 8/2015

OTHER PUBLICATIONS

PCT International Search Report for PCT/EP2017/058487, dated Jul. 18, 2017 (6 pages).
(Continued)

*Primary Examiner* — Christian Jang
(74) *Attorney, Agent, or Firm* — Maginot, Moore & Beck LLP

(57) ABSTRACT

A blood pressure and cardiac monitoring system includes a sensing assembly, a processor, a memory, a communication interface, and any suitable computer implemented modules communicatively coupled to each other via a bus. The sensing assembly comprises of a first sensor (single or multi-axes) located at a first axis of a target generating a first time-dependent motion waveform representative of one or more contractile properties of the target's heart and a second sensor (single or multi-axes) located at a second axis of the target generating a second time dependent motion waveform representative of the target's blood flow. The first and second sensor can be integrated in a multi-axes sensor which sense both the axes. The processor is configured to receive the first time dependent motion waveform and the second time dependent motion waveform, and to determine a first time difference between a vital sign present in the first time dependent motion waveform and the second time dependent motion waveform. A third sensor located along any axis of the target generating a third time dependent waveform representative of the electrical potential due to the depolarization of heart muscle is provided. At least one of the
(Continued)

sensors may be added or configured to either remove motion artifacts (as a reference sensor) or detect attributes from the environment for providing context awareness information.

4 Claims, 4 Drawing Sheets

Related U.S. Application Data

(60) Provisional application No. 62/319,920, filed on Apr. 8, 2016.

(51) Int. Cl.

| | |
|---|---|
| *A61B 5/11* | (2006.01) |
| *G16H 50/20* | (2018.01) |
| *G16H 10/60* | (2018.01) |
| *A61B 5/00* | (2006.01) |
| *A61B 5/0295* | (2006.01) |
| *A61B 5/024* | (2006.01) |
| *A61B 5/0285* | (2006.01) |
| *A61B 5/316* | (2021.01) |
| *A61B 5/318* | (2021.01) |
| *A61B 5/352* | (2021.01) |
| *A61B 5/0205* | (2006.01) |
| *A61B 8/04* | (2006.01) |

(52) U.S. Cl.
CPC ........ *A61B 5/0295* (2013.01); *A61B 5/02108* (2013.01); *A61B 5/02125* (2013.01); *A61B 5/1107* (2013.01); *G16H 10/60* (2018.01); *G16H 50/20* (2018.01); *A61B 5/0002* (2013.01); *A61B 5/0205* (2013.01); *A61B 5/0285* (2013.01); *A61B 5/02416* (2013.01); *A61B 5/1102* (2013.01); *A61B 5/316* (2021.01); *A61B 5/318* (2021.01); *A61B 5/352* (2021.01); *A61B 5/72* (2013.01); *A61B 8/04* (2013.01); *A61B 2562/0219* (2013.01)

(56) References Cited

U.S. PATENT DOCUMENTS

2015/0196213 A1* 7/2015 Pandia ................ A61B 5/1102 600/509
2016/0081563 A1 3/2016 Wiard et al.

OTHER PUBLICATIONS

PCT Written Opinion for PCT/EP2017/058487, dated Jul. 18, 2017 (5 pages).

* cited by examiner

BLOOD PRESSURE AND CARDIAC MONITORING SYSTEM AND METHOD THEREOF

CROSS-REFERENCE TO RELATED APPLICATIONS

This application is a continuation-in-part of U.S. patent application Ser. No. 15/564,585, filed Oct. 5, 2017, which claims the benefit of U.S. Provisional Application No. 62/319,920, filed Apr. 8, 2016, which are incorporated herein by reference.

FIELD

This disclosure is related to health monitoring devices, and more particularly, to a blood pressure and cardiac monitoring system and method for monitoring vital signs.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of the disclosure related to a blood pressure and cardiac monitoring system are described. For example, the system comprises a sensing assembly and a processor communicatively coupled to the sensing assembly. The sensing assembly located at a first axis of a target generating a first time-dependent motion waveform representative of one or more contractile properties of the target's heart and further located at a second axis of the target generating a second time dependent motion waveform representative of the target's blood flow. The processor configured to receive the first time dependent motion waveform and the second time dependent motion waveform, and to determine a first time difference between a vital sign present in the first time dependent motion waveform and the second time dependent motion waveform.

The sensing assembly comprises a first sensor located on the first axis and second axis of the target and a second sensor located along any axis of the target generating a third time dependent waveform representative of the electrical potential due to the depolarization of heart muscle. The blood pressure and cardiac monitoring system may be either integrated into a client device or communicatively coupled to at least one of a client device, a server, and a network. The client device is a cloud computing device. The sensing assembly is selected from a group consisting of an accelerometer, a motion sensor, an optical sensor, a transducer, a Doppler ultrasonic transducer, an acoustic sensor, an electrode, an ECG sensor, a sonar sensor, a thermal sensor, an environmental sensor, and a target orientation sensor.

According to another aspect of the disclosure, a sensing assembly for monitoring vital signs comprises a multi-sensing axis located at a first axis of a target generating a first time-dependent motion waveform representative of one or more contractile properties of the target's heart, the multi-sensing axis further located at a second axis of the target generating a second time dependent motion waveform representative of the target's blood flow and a processor configured to receive the first time dependent motion waveform and the second time dependent motion waveform, the processor configured to determine first time difference between a vital sign present in the first time dependent motion waveform and the second time dependent motion waveform.

The sensing assembly further comprises a sensor located along any axis of the target generating a third time dependent waveform representative of the electrical potential due to the depolarization of heart muscle. The assembly is integrated into a health monitoring device and the processor is communicatively coupled to the health monitoring device. The health monitoring device that is a cloud computing device is communicatively coupled to at least one of a client device, a server, and a network.

The sensing assembly is selected from a group consisting of an accelerometer, a motion sensor, an optical sensor, a transducer, a Doppler ultrasonic transducer, an acoustic sensor, an electrode, an ECG sensor, a sonar sensor, a thermal sensor, an environmental sensor, and a target orientation sensor.

According to another aspect of the disclosure, a method comprises generating a first time-dependent motion waveform, using a sensing assembly, representative of one or more contractile properties of the target's heart, generating a second time dependent motion waveform, using the sensing assembly, representative of the target's blood flow, and a processor configured to receive the first time dependent motion waveform and the second time dependent motion waveform, the processor configured to determine a first time difference between a vital sign present in the first time dependent motion waveform and the second time dependent motion waveform.

The method further comprises positioning the sensing assembly on a first axis and a second axis of the target for generating the first time-dependent motion waveform and the second time-dependent motion waveform.

The method further comprises generating a third time dependent waveform, by positioning a second sensor located along any axis of the target, representative of the electrical potential due to the depolarization of heart muscle.

BRIEF DESCRIPTION OF THE DRAWINGS

These and other features, aspects, and advantages of this disclosure will become better understood when the following detailed description of certain exemplary embodiments is read with reference to the accompanying drawings in which like characters represent like arts throughout the drawings, wherein.

DETAILED DESCRIPTION

Figure 1:
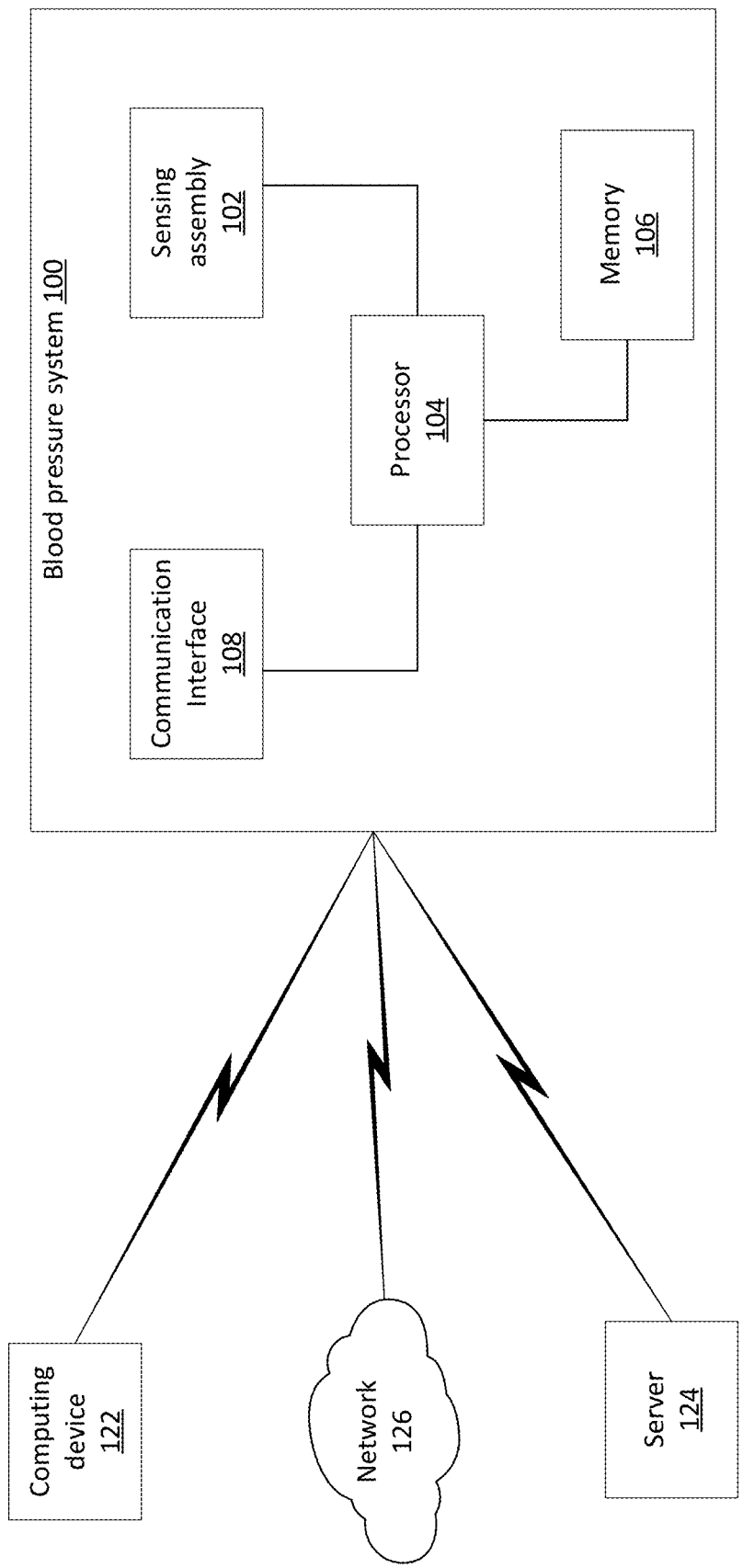
FIG. 1 illustrates a block diagram of a blood pressure monitoring system according to an exemplary embodiment of a disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such development effort might be complex and time consuming, but would nevertheless be a routine undertaking of design, fabrication, and manufacture for those of ordinary skill having the benefit of this disclosure.

The following description is presented to enable any person skilled in the art to make and use the described embodiments, and is provided in the context of a particular application and its requirements. Various modifications to the described embodiments will be readily apparent to those skilled in the art, and the general principles defined herein may be applied to other embodiments and applications without departing from the spirit and scope of the described embodiments. Thus, the described embodiments are not limited to the embodiments shown, but are to be accorded the widest scope consistent with the principles and features disclosed herein.

As used herein, the term "electrocardiography (ECG)" refers to the changes of the electrical potential due to the depolarization of heart muscle. R-peak of the ECG signal can be used in the calculation of time intervals for monitoring blood pressure (e.g. RJ-time interval), R-peak or Q-peak of ECG signal for monitoring cardiac activity (e.g. pre-ejection period (PEP) and its influencing parameters such as hormones, preload, afterload, etc.) or as the trigger to start data measurement/analysis. The term "seismocardiography (SCG)" refers to the acceleration of the sternum caused by the cardiac activity of the heart while the term "ballistocardiography (BCG)" refers to the changes in the center of mass of the body due to blood flow or heart activity. As used herein, a new term is introduced here. The term "Mass Transit Time (MTT)" refers to the time interval between the start of the blood ejection from the heart to the time where blood turns at the arches of the aorta or any other specific locations where the change in the blood flow can be detected. It is not a pulse transit time because we are not detecting the transit of the pulse but the transit of the mass of blood and the resulting impulse of the mass movement to the torso of the body. Therefore, it is called mass transit time and not pulse transit time. The J-peak of the RJ-time interval comes from the peak obtained from either SCG or BCG. In an example case where a tri-axis accelerometer is used for SCG measurement, the J-peak of the SCG is labelled as $J_X$-peak for acceleration in the X-axis (also referred as head-to-foot axis), $J_Y$-peak in Y-axis (also referred as right-left axis) and $J_Z$-peak for acceleration in the Z-axis (also referred as dorso-ventral axis). For simplicity, for use herein, $J_Z$-peak can refer to any point on the Z-axis acceleration or as labelled in FIG. 4 as $J_{z1}$-, $J_{z2}$-, or $J_{z3}$-peak as an example, for better or easier peak detection in the algorithm. Accelerometer signal detected on Z-axis (also referred as dorso-ventral axis) measures the chest movement due to heart contraction. $J_Z$-peak can be used with ECG signal (e.g. R-$J_Z$, or Q-$J_Z$ time interval) to investigate important cardiac activity such as the pre-ejection period (PEP) and its influencing parameters such as hormones, preload, afterload, etc. Accelerometer signal detected on X-axis (also referred as head-to-foot axis) measures the body recoil movement due to blood flow. $J_X$-peak signifies the time where blood pumps out from the heart and reaches the arches of Aorta blood vessel. One example will be R-$J_X$ time interval for blood pressure monitoring. In the measurement of the time intervals, R-peak of ECG or $J_Z$-peak of accelerometer can be used to trigger the start of measurement.

The blood pressure monitoring can also be performed solely using SCG or accelerometers (e.g. $J_Z$-$J_X$ time interval). Again here, $J_Z$-peak refers to either $J_{z1}$-peak or $J_{z2}$-peak or $J_{z3}$-peak or any other points along Z-axis, and is used depending on which gives a better or easier detection. For example, $J_{z1}$-peak signifies the time where heart contracts while $J_{z3}$-peak signifies the time where blood starts rushes out of the heart and $J_X$-peak signifies the time where the blood rushes through the arches of the Aorta blood vessel. This time interval is inversely correlated to the blood pressure. $J_Z$-peak can also be used as the trigger to start data measurement/analysis. $J_X$-peak can be used in the calculation of time intervals for monitoring blood pressure (e.g. R-$J_X$ time interval, $J_Z$-$J_X$ time interval, or $J_X$ with photoplethysmogram (PPG) signal time interval). The term "photoplethysmography (PPG)" refers to the changes in light adsorption in blood. Depending on the position where the PPG data is taken, the time interval between R-peak with PPG, $J_Z$-peak (from SCG) with PPG, $J_X$-peak (from SCG) with PPG, PPG in one location with PPG in another location, can be used to monitor blood pressure or blood flow velocity.

FIG. 1 illustrates an exemplary embodiment of a blood pressure monitoring system 100. The system 100 can be either removably worn by a target, i.e. a patient, applied to, or placed at a sternum of the target and configured to either continuously, semi-continuously, or synchronously detected at least one signal. In some embodiments, the system 100 can be implanted into the target. In another embodiment, the system 100 can be integrated into a client device either worn by the target, applied to, or positioned placed at the sternum of the target and configured to either continuously, semi-continuously, or synchronously detected at least one signal. As some examples, the client device may be a patch, a neckless, a chest strap, a pendant, or any suitable device. If the system 100 is implantable into the target, the system 100 may be a pacemaker, or any suitable implantable device. The system 100 includes a sensing assembly 102, a processor 104, a memory 106, a communication interface 108, and any suitable computer implemented modules communicatively coupled to each other via a bus. A housing may be provided to encapsulate at least one or more of the sensing assembly 102, the processor 104, the memory 106, and the communication interface 108. In one embodiment, the housing may be formed from a thin film material that allows the target to stretch, bend, twist, squeeze, fold, expand, or combination thereof either worn by the target, applied to, reapplied to, removed from, or positioned placed at the sternum of the target. The memory 106 communicatively coupled to the processor 104 stores computer-readable instructions that, when executed by the processor 104 of the system 100, causes the system, and more particularly the processor 104, to perform or monitor vital signs and cardiac activity based on the detected signal transmitted by the sensing assembly 102. The memory 106 may include any transitory, non-transitory, volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. The vital signs include body temperature, pulse rate, blood pressure, blood speed, and respiratory rate.

The processor 104 may be of any type, including but not limited to a microprocessor, a microcontroller, a digital signal processor, or any combination thereof. The processor 104 may include one or more levels of caching, such as a level cache memory, one or more processor cores, and registers. Depending on the desired configuration, the processor may be of any type, including but not limited to a microprocessor (µP) a microcontroller (µC), a digital signal processor (DSP), or any combination thereof. The processor may include one or more levels of caching, such as a level cache memory, one or more processor cores, and registers. The example processor cores may (each) include an arithmetic logic unit (ALU), a floating point unit (FPU), a digital signal processing core (DSP Core), or any combination thereof. An example memory controller may also be used with the processor, or in some implementations the memory controller may be an internal part of the processor. The communication interface 108 allows software and data to be transferred between a computer system external to the system 100 and the system in the form of signals which may be, for example, electronic, electromagnetic, optical, or other signals capable of being received by the communication interface. The communication interface may be for example a modem, a network interface, a communication port, a PCM-CIA slot and card, or the like. The sensing assembly 102 is configured to detect at least one or more of electrocardiogram (ECG) signal, a first motion signal, a second motion signal, a photoplethysmorgram (PPG) signal, seismocardiogram signal (SCG) and ballistocardiogram (BCG) signal. In one embodiment, the sensing assembly 102 is a single-axis sensing assembly. In another embodiment, the sensing assembly 102 is a double-axis sensing assembly. In yet another embodiment, the sensing assembly 102 is a multi-axis assembly. As an example, the sensing assembly 102 includes at least one sensor device. The sensor device may be an accelerometer, a motion sensor, an optical sensor, a transducer, a Doppler ultrasonic transducer, an acoustic sensor, an electrode, an ECG sensor, a target orientation sensor, a sonar sensor, a thermal sensor, an environmental sensor, and any suitable sensor or transducer. As an example, a first sensor device located at a first axis of the target for detecting a first time-dependent motion waveform representative of one or more contractile properties of the target's heart and a second sensor device located at a second axis of the target for detecting a second time dependent motion waveform representative of the target's blood flow. As another example, a multi-axes sensor device located at both first and second axis of the target for detecting a first time-dependent motion waveform representative of one or more contractile properties of the target's heart and for detecting a second time dependent motion waveform representative of the target's blood flow. In some embodiment, the sensing assembly comprises a first sensing axis located at a first axis of a target generating a first time-dependent motion waveform representative of one or more contractile properties of the target's heart and a second sensing axis located at a second axis of the target generating a second time dependent motion waveform representative of the target's blood flow. Additional sensors provided at a location along any axis of the target to either remove motion artifacts (as a reference sensor) or detect attributes from the environment for providing context awareness information.

The system 100 may be a wired computing system or a wireless computing system. In one embodiment, the system 100 is a cloud computing device which may be communicated with via the Internet, and which may be co-located or geographically distributed, wherein shared resources, software, and information are provided to computers and other devices on demand for example, as will be appreciated by those skilled in the art. In another embodiment, the cloud blood pressure system 100 may be implemented as one or more servers which may be communicated with via the Internet. The system 100 may communicatively couple to a computing device 122, a server 124, or a network 126 via one or more links. The link may be wired, wireless, or combination thereof. The wireless communication link may include cellular protocol, data packet protocol, radio frequency protocol, satellite band, infrared channel, or any other protocol able to transmit data among client machines. The wired communication link may include any wired line link.

Depending on the application, one or more servers may be communicatively coupled to the computing device 122 to and the system 100. The server 124 may be an application server, a certificate server, a mobile information server, an e-commerce server, a FTP server, a directory server, CMS server, a printer server, a management server, a mail server, a public/private access server, a real-time communication server, a database server, a proxy server, a streaming media server, or the like. The client machine 122 may be a personal computer or desktop computer, a laptop, a cellular or smart phone, a tablet, a personal digital assistant (PDA), a gaming console, an audio device, a video device, an entertainment device such as a television, a vehicle infotainment, a wearable device, a thin client system, a thick client system, or the like. The client machine 122 can in some embodiment be referred to as a single client machine or a single group of client machines, while the server 124 may be referred to as a single server or a single group of servers. In one embodiment a single client machine communicates with more than one server, while in another embodiment a single server communicates with more than one client machine. In yet another embodiment, a single client machine communicates with a single server. The network 126 can comprise one or more sub-networks, and can be installed between any combination of the client machines 122 and the server 124. In some embodiments, the network 126 can be for example a local-area network (LAN), a metropolitan area network (MAN), a wide area network (WAN), a primary network 126 comprised of multiple sub-networks located between the client machines 122 and the server 124. Still further embodiments include the network 126 that can be any network types such as a point to point network, a broadcast network, a telecommunication network, a data communication network, a computer network, an ATM (Asynchronous Transfer Mode) network, a SONET (Synchronous Optical Network) network, a SDH (Synchronous Digital Hierarchy) network, a wireless network, a wireline network, and the like. Depending on the application, other networks may be used so that data exchanged between the client machine and the server can be transmitted over the network. Network topology of the network 124 can differ within different embodiments which may include a bus network topology, a star network topology, a ring network topology, a repeater-based network topology, or a tiered-star network topology. Additional embodiments may include a network of mobile telephone networks that use a protocol to communicate among mobile devices, where the protocol can be tier example AMPS, TDMA, CDMA, GSM, GPRS, UNITS, LTE or any other protocol able to transmit data among mobile devices.

Figure 2:
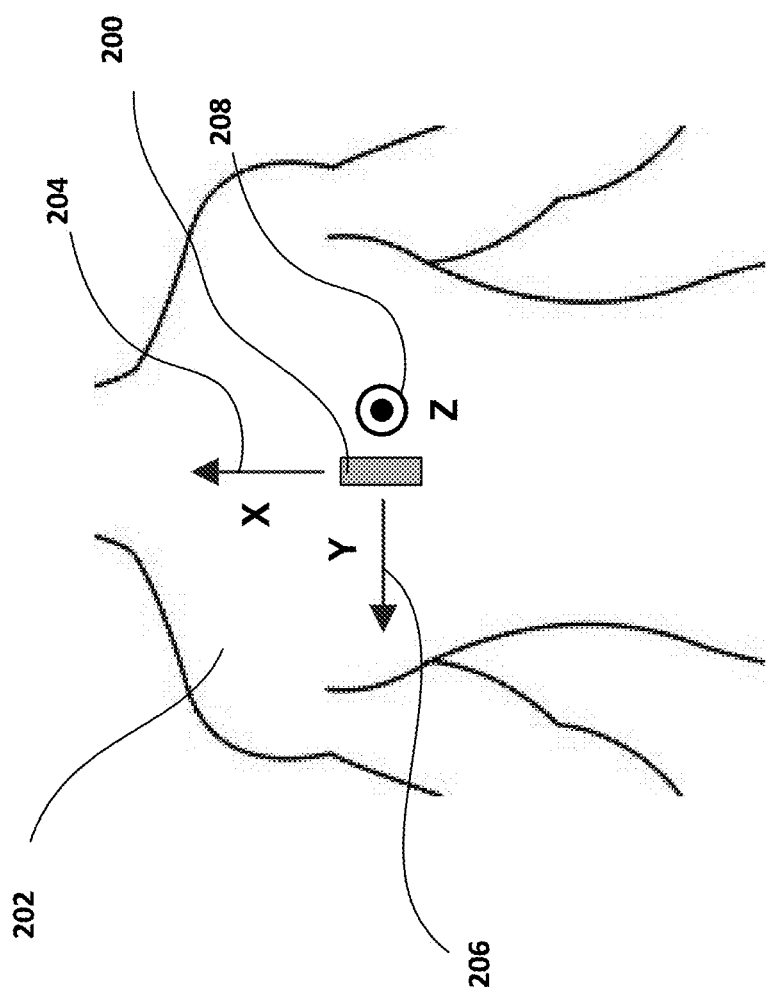
FIG. 2 illustrates a target with a blood pressure monitoring system of FIG. 1 placed on a sternum of the target according to a described embodiment of the disclosure.

FIG. 2 illustrates a target 202, such as a user or a patient, with a blood pressure monitoring system 200 according to a described embodiment of the disclosure. The system 200 identical to the system 100 depicted in FIG. 1 is placed on a sternum of the target and configured to continuously, semi-continuously, or synchronously detect or monitor at least one or more of electrocardiogram (ECG) signal, a first motion signal, a second motion signal, a photoplethysmorgram (PPG) signal, a seismocardiogram (SCG) signal, a ballistocardiogram (BCG) signal or environmental signal. In some embodiments, the system 200 is placed on the sternum of the target for sensing movement of the chest wall. Since bones can transfer the body movement due to cardiac activities with less damping effects than muscles, the system 200 is able to detect the signal that is less affected by motion artifacts. In another embodiment, the system 100 may be placed on any location of the body proximal to the sternum of the target. In yet another embodiment, the system 200 is configured to detect the time interval between heart contraction and blood flow. As illustrated, X-axis 204, Y-axis 206, and Z-axis 208 are provided. A first sensor device of the system 100 located at a first axis of the target for continuously detecting a first time-dependent motion waveform representative of one or more contractile properties of the target's heart and a second sensor device located at a second axis of the target for continuously detecting a second time dependent motion waveform representative of the target's blood flow. The first axis is the dorso-ventral axis and the second axis is the head-to-foot axis. The axis can be interchangeable between x, y, and z depending on position arrangement of the system 200. If the system 200 is pointing at X-axis 204, as illustrated in FIG. 2 the first axis is the Z-axis 208 and the second axis is the X-axis 204. In another embodiment, the system 200 is pointing at Y-axis 206, the first axis is the Z-axis 208 and the second axis is the Y-axis 206. The sensor devices may be a single-axis sensor device or a double-axis sensor device. In another embodiment, the sensor device is a multi-axis sensor device configured to map the resulting vector along the axis of interest, e.g. if the multi-axis sensor device is rotated and not completely aligned with for example the head-to-foot axis. As illustrated, the first and second sensor devices are accelerometers. In another embodiments, a multi-axes can be placed on both the first, second and third axis of the target. At the first axis, a first time-dependent motion waveform representative of one or more contractile properties of the target's heart is generated. At the second axis, a second time-dependent motion waveform representative of the target's blood flow is generated. And at the third axis, the data is used to map the resulting vector of axis of interest, e.g. if the sensor is rotated and not completely aligned with for example the head-to-foot axis.

Figure 3:
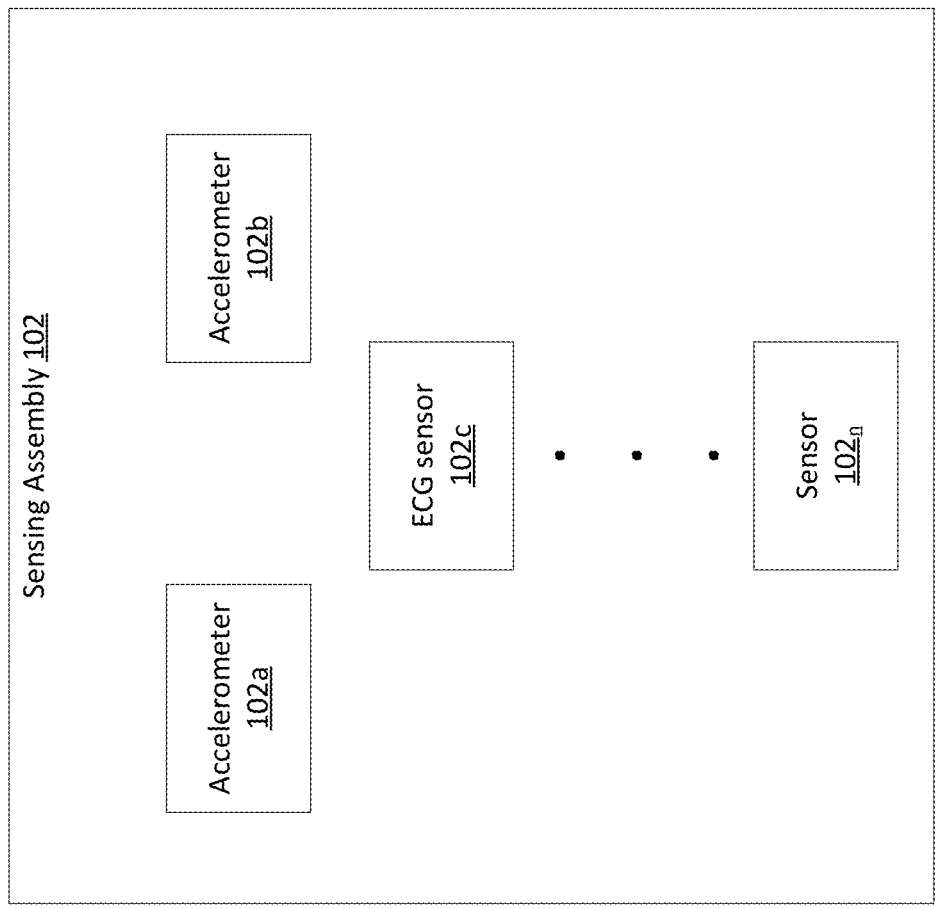
FIG. 3 illustrates a sensing assembly for the blood pressure monitoring system of FIG. 1 according to a described embodiment of the disclosure.

FIG. 3 illustrates a sensing assembly 102 for the blood pressure monitoring system 100. The sensing assembly 102 is configured to detect at least one or more of electrocardiogram (ECG) signal, a first motion signal, a second motion signal, a photoplethysmorgram (PPG) signal, seismocardiogram (SCG) signal and ballistocardiogram (BCG) signal. In one embodiment, the sensing assembly 102 is a single-axis sensing assembly. In another embodiment, the sensing assembly 102 is a double-axis sensing assembly. In yet another embodiment, the sensing assembly 102 is a multi-axis assembly. As an example, the sensing assembly 102 includes at least one sensor device. The sensor device may be an accelerometer, a motion sensor, an optical sensor, a transducer, a Doppler ultrasonic transducer, an acoustic sensor, an electrode, an ECG sensor, a target orientation sensor, a sonar sensor, a thermal sensor, an environmental sensor, and any suitable sensor or transducer. As an example, a first sensor device located at a first axis of the target generates a first time-dependent motion waveform representative of one or more contractile properties of the target's heart and a second sensor device located at a second axis of the target generates a second time dependent motion waveform representative of the target's blood flow. As another example, a third sensor device located at any axis of the target generates a third time dependent waveform representative of the electrical potential due to the depolarization of heart muscle. In one embodiment, the first and second sensor devices are accelerometers 102a, 102b and the third sensor device 102c is either an electrode or an ECG sensor. In another embodiment, a fourth sensor located along any axis of the target is provided and is configured to either detect attributes from the environment for providing context awareness information or remove motion artifacts (as reference sensor). In another embodiment, the first sensor and second sensor is integrated into multi-axes sensor (102a and 102b integrated in a multi-axes sensor).

Figure 4:
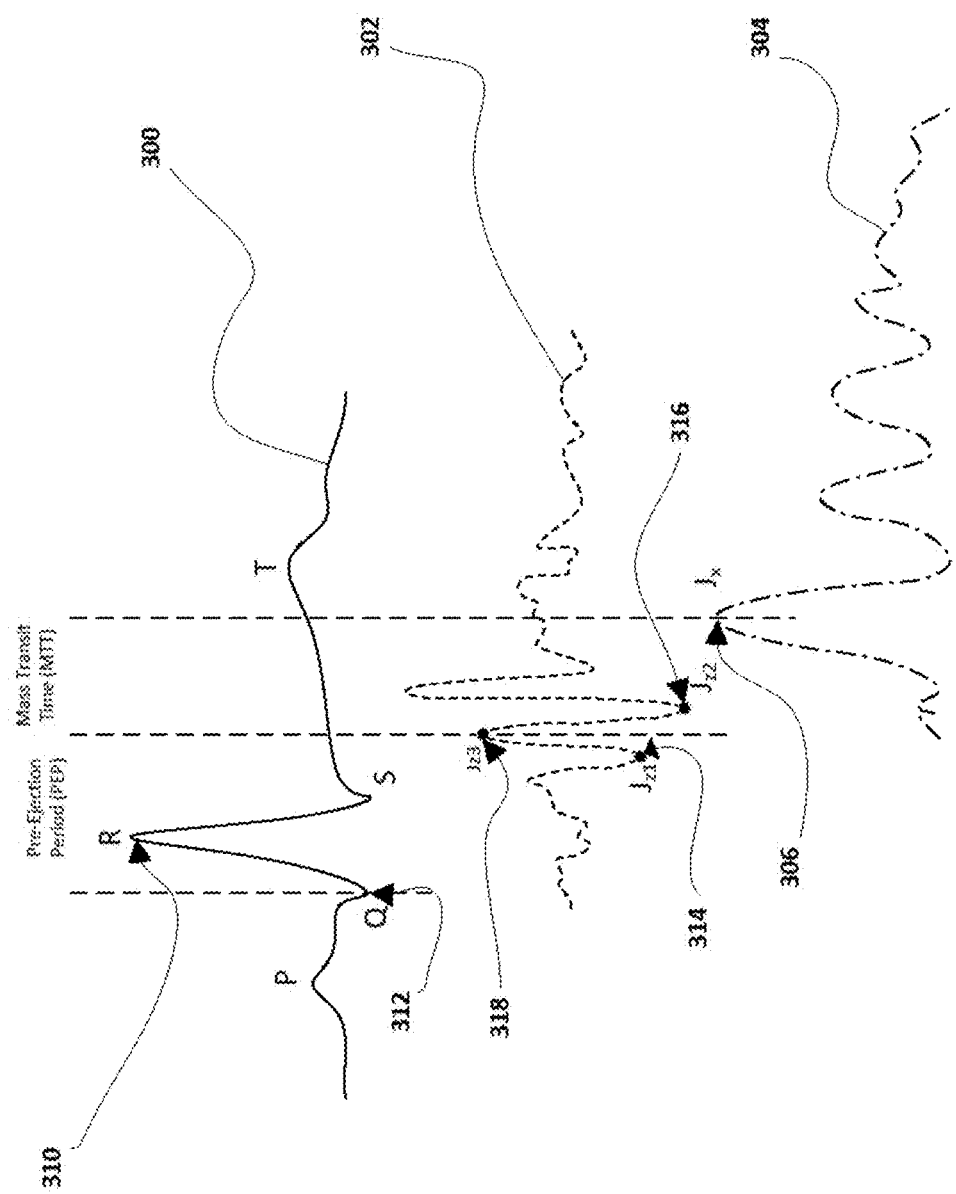
FIG. 4 illustrates a graph of time-dependent waveforms according to an exemplary embodiment of the disclosure.

FIG. 4 illustrates time-dependent waveforms, ECG waveform 300, a first motion waveform 302, and a second motion waveform 304 continuously monitored by the blood pressure system to determine the target's vital sign, i.e. blood pressure and cardiac activity (e.g. PEP and its influencing parameters). The ECG waveform 300, generated by the ECG sensor 102c of the sensing assembly 102 placed on the target represents the electrical excitation of the heart, features a peak 310. The first motion waveform 302 generated by the first accelerometer 102a of the sensing assembly 102 represents the chest movement due to the heart contraction or the cardiac activity of the heart. In one embodiment, the first motion waveform 302 is a SCG waveform in the Z-axis. In another embodiment, the first motion waveform 302 is a BCG waveform in the Z-axis. The second motion waveform 304, generated by the second accelerometer 102b of the sensing assembly 102 represents the body recoil movement due to the blood flow, features a peak 306. In one embodiment, the second motion waveform 304 is a SCG waveform in the X-axis. In another embodiment, the second motion waveform 304 is a BCG waveform in the X-axis. In another embodiment, the first motion waveform 302 and the second motion waveform 304 is generated by a multi-axes sensor (e.g. an accelerometer) located at both the first and second axis of the target. In another embodiment, one multi-axes sensor is used at each axis (first and second or third), to generate a combined data of all three axes (X, Y, Z) for better performance. The peak 310 also referred as R-peak of ECG waveform 300 may be used either in the calculation of time intervals for monitoring blood pressure, vital signs and cardiac activity or to trigger a start of blood pressure measurement. The peak 312 also referred as Q-peak of ECG waveform 300 may also be used in the calculation of time intervals for monitoring blood pressure, vital signs and cardiac activity or to trigger a start of blood pressure measurement. Any points along the first motion waveform 302 may be used in calculation of time intervals for monitoring blood pressure, vital signs and cardiac activity or to trigger a start of blood pressure measurement. As an example, the peak 314 may be used in calculation of time intervals for monitoring blood pressure, vital signs and cardiac activity or to trigger a start of blood pressure measurement. As another example, the peak 316 may be used in calculation of time intervals for monitoring blood pressure, vital signs and cardiac activity or to trigger a start of blood pressure measurement. As another example, the peak 318 may be used in calculation of time intervals for monitoring blood pressure, vital signs and cardiac activity or to trigger a start of blood pressure measurement. Any points along second motion waveform 304 may be used in the calculation of time intervals for monitoring blood pressure, vital signs and cardiac activity. As one example, the peak 306 may be used in the calculation of time intervals for monitoring blood pressure, vital signs and cardiac activity. In one embodiment, the time difference between the peaks 306, 310 is the combination of the pre-ejection period (PEP) plus the mass transit time (MTT). In another embodiment, the time difference between any points 312 located along the ECG waveform 300 and the peak 306 of the second motion waveform 304 features the PEP+MTT time interval. As an example, the point 312 is located at Q. As described previously, pre-ejection period (PEP) is defined between two points located along waveforms 300, 302. In one embodiment, $J_{z1}$-peak 314 located along the waveform 302 can be used with point Q 312 along the ECG waveform 300 to investigate important cardiac activity such as the pre-ejection period (PEP) and its influencing parameters such as hormones, preload, afterload, etc. In yet another embodiment, $J_{z2}$-peak 316 located along the waveform 302 can be used with point Q 312 along the ECG waveform 300 to investigate important cardiac activity such as the pre-ejection period (PEP) and its influencing parameters such as hormones, preload, afterload, etc. In yet another embodiment, $J_{z3}$-peak 318 located along the waveform 302 can be used with point Q 312 along the ECG waveform 300 to investigate important cardiac activity such as the pre-ejection period (PEP) and its influencing parameters such as hormones, preload, afterload, etc. In yet another embodiment, $J_{z1}$-peak 314 located along the waveform 302 can be used with peak R 310 along the ECG waveform 300 to investigate important cardiac activity such as the pre-ejection period (PEP) and its influencing parameters such as hormones, preload, afterload, etc. In further yet another embodiment, $J_{z2}$-peak 316 located along the waveform 302 can be used with peak R 310 along the ECG waveform 300 to investigate important cardiac activity such as the pre-ejection period (PEP) and its influencing parameters such as hormones, preload, afterload, etc. In further yet another embodiment, $J_{z3}$-peak 318 located along the waveform 302 can be used with peak R 310 along the ECG waveform 300 to investigate important cardiac activity such as the pre-ejection period (PEP) and its influencing parameters such as hormones, preload, afterload, etc. As one embodiment, the time difference between $J_{z1}$-peak 314 of the waveform 302 and the peak 306 of the waveform 304 features the mass transit time (MTT). As another embodiment, the time difference between $J_{z2}$-peak 316 of the waveform 302 and the peak 306 of the waveform 304 features the mass transit time (MTT). In yet another embodiment, the time difference between $J_{z3}$-peak 318 of the waveform 302 and the peak 306 of the waveform 304 features the mass transit time (MTT).

The time interval between the $J_z$ peak of the dorso-ventral axis to the $J_x$-peak of the head-to-foot axis signifies the time it takes for the heart to start contracting till the time the blood flow reaches the arches of the aorta. This $J_z$-$J_x$ time interval can be used to monitor blood pressure or relative blood pressure. The time interval can also be used to monitor other cardiovascular parameters such as arterial stiffness, as one example or cardiac output as another example.

As described above, blood pressure can be monitored by measuring the blood flow velocity profile of two PPG signals at two different locations at the time intervals. Alternatively, the blood flow velocity can be measured using a Doppler ultrasonic transducer. This method uses reflection of ultrasonic irradiation of frequency $f_0$ from the blood in any arteries, e.g. the Aorta, with additional ultrasonic frequencies appearing in the reflected wave spectrum as sidebands at spectral position $f_0+/-\Delta f$, with $\Delta f$ being a time-dependent function of blood velocity $v(t)$:

$$\Delta f(t) = \Delta f(v) = \Delta f(v(t))$$

The peak reading of $\Delta f$ or its amplitude $\Delta f_A$ corresponds to the peak velocity $v_A$ of the blood ejected from the heart into the aorta, and has a correlation to blood pressure. $\Delta f_A$ or $v_A$ corresponds to the systolic blood pressure.

The minimum reading of $\Delta f$ in between 2 maxima $\Delta f_A$, namely $\Delta f_{min}$ has a correlation to the minimum blood velocity $v_{min}$ and to blood pressure as well. $\Delta f_{min}$ or $v_{min}$ corresponds to the diastolic blood pressure.

The measurement of $\Delta f$ can be done by synchronous demodulation of the reflected ultrasonic signal spectrum with the center frequency $f_0$ into the base-band, by a combination of mixing stage and low-pass filter, or any suitable FM-demodulation technique. Phase-locked loop demodulators, ratio-detectors, and any suitable active components, depending on the applications, may be used.

In yet another embodiment, the sensor device may be any suitable piezoelectric or electrostatic/capacitive bending actuator or bimorph configured to convert an electrical carrier frequency signal at $f_0$ into an ultrasonic wave, and an incoming ultrasonic wave spectrum is converted back to an electrical signal spectrum for further analysis. In addition, at least one accelerometer signal can be used, depending on the application, to trigger the ultrasonic irradiation and evaluation loop, for cross-correlating data, and for providing context-awareness information. More than one accelerometer of the system 200 can also be used to detect if the user is moving or the kind of activity the user is doing, to add additional information to the user. The additional accelerometer can also be utilized to reduce/filter motion artifacts from the $J_x$ or $J_z$ data.

The embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling with the sprit and scope of this disclosure.

While the patent has been described with reference to various embodiments, it will be understood that these embodiments are illustrative and that the scope of the disclosure is not limited to them. Many variations, modifications, additions, and improvements are possible. More generally, embodiments in accordance with the patent have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A method comprising:
  generating a first time dependent motion waveform, using a sensing assembly positioned on a sternum of a target, the first time dependent motion waveform representative of one or more contractile properties of the target's heart;
  generating a second time dependent motion waveform, using the positioned sensing assembly, the second time dependent motion waveform representative of the target's blood flow;
  receiving the first time dependent motion waveform and the second time dependent motion waveform with a processor;
  determining a time difference between a first vital sign present in the first time dependent motion waveform and a second vital sign present in the second time dependent motion waveform using the processor; and measuring blood pressure, blood flow, and/or cardiac activity of the target based on the determined time difference, wherein the first vital sign is a first peak in the first time dependent motion waveform corresponding to an end of a pre-ejection period, and wherein the second vital sign is a second peak in the second time dependent motion waveform occurring after the end of the pre-ejection period.

2. The method of claim 1 further comprising:

positioning the sensing assembly on a first axis and a second axis of the target for generating the first time dependent motion waveform and the second time dependent motion waveform.

3. The method of claim 2 wherein:

the positioned sensing assembly includes a first sensor located on the first axis and the second axis, the method further comprises generating a third time dependent waveform using a second sensor of the sensing assembly, and the third time dependent waveform is representative of an electrical potential due to the depolarization of heart muscle of the target.

4. The method of claim 1, wherein the determined time difference corresponds to a mass transit time representing a time interval from a start of an ejection of a mass of blood from the target's heart to when the mass of blood turns at arches of the target's aorta.

* * * * *